(12) United States Patent
Azar et al.

(10) Patent No.: US 7,066,929 B1
(45) Date of Patent: Jun. 27, 2006

(54) SELECTIVE PHOTOTHERMOLYSIS

(75) Inventors: Zion Azar, Shoham (IL); Pinchas Shalev, Kfar-Saba (IL)

(73) Assignee: Radiancy Inc., Orangeburg, NY (US)

( * ) Notice: Subject to any disclaimer, the term of this patent is extended or adjusted under 35 U.S.C. 154(b) by 0 days.

(21) Appl. No.: 10/148,740

(22) PCT Filed: Dec. 2, 1999

(86) PCT No.: PCT/IL99/00658

§ 371 (c)(1),
(2), (4) Date: May 30, 2002

(87) PCT Pub. No.: WO01/39834

PCT Pub. Date: Jun. 7, 2001

(51) Int. Cl.
*A61B 18/18* (2006.01)

(52) U.S. Cl. ............................ 606/9; 606/10; 607/89
(58) Field of Classification Search .............. 606/9; 607/89
See application file for complete search history.

(56) References Cited

U.S. PATENT DOCUMENTS

| | | | |
|---|---|---|---|
| 5,339,347 A | | 8/1994 | Slatkin et al. |
| 5,405,368 A | * | 4/1995 | Eckhouse .................. 606/9 |
| 5,501,655 A | * | 3/1996 | Rolt et al. .................. 607/154 |
| 5,595,568 A | | 1/1997 | Anderson et al. |
| 5,629,967 A | * | 5/1997 | Leksell et al. .............. 378/65 |
| 5,746,735 A | | 5/1998 | Furumoto et al. |
| 5,759,200 A | | 6/1998 | Azar |
| 5,814,040 A | | 9/1998 | Nelson et al. |
| 5,879,376 A | * | 3/1999 | Miller ........................ 606/9 |
| 5,885,274 A | * | 3/1999 | Fullmer et al. ............. 606/9 |
| 5,894,503 A | * | 4/1999 | Shepherd et al. .......... 378/203 |
| 6,045,548 A | * | 4/2000 | Furumoto et al. ......... 606/9 |
| 6,084,717 A | * | 7/2000 | Wood et al. ............... 606/18 |
| 6,214,034 B1 | * | 4/2001 | Azar ........................... 606/9 |
| 6,475,211 B1 | | 11/2002 | Chess et al. |
| 6,512,813 B1 | * | 1/2003 | Krispel et al. ............. 378/65 |
| 6,520,959 B1 | * | 2/2003 | Iwahashi et al. ........... 606/13 |
| 6,569,157 B1 | | 5/2003 | Shain et al. |

FOREIGN PATENT DOCUMENTS

| | | |
|---|---|---|
| GB | 2 126 901 | 4/1984 |
| WO | WO 91/15624 | 10/1991 |
| WO | WO 93/21842 | 11/1993 |
| WO | WO 96/17656 | 6/1996 |
| WO | WO 99/58195 | 11/1999 |

OTHER PUBLICATIONS

Anderson,R.R. et al.; "Selective Photothermolysis:Precise Microsurgery by Selective Absorption of Pulsed Radiation;" Apr. 29, 1983; Science; vol. 220;pp. 524–527.

Frysh, H.; "Chemistry of Bleaching;" Complete Dental Bleaching;Chapter 2; pp. 25–33; Quintessence Publishing Co., Inc.

Pope,K. for LaserTraining.com; "Epidermal Protection Factor—Candela's Dynamic Cooling Device;" Mar., 1999; pp. 1–6; retrieved from Internet: <www.lasertraining.com/med–30.htm>.

Tian Tan, O. et al.; "585 nm for the Treatment of Port–Wine Stains;" Dec. 1990; Plastic and Reconstructive Surgery; vol. 86; No. 6; pp. 1112–1117.

Welch, A.J. et al.; "Evaluation of Cooling Techniques for the Protection of the Epidermis During ND–YAG Laser Irradiation of Skin;" 1983; Neodymium–YAGLaser in Medicine;Joffe,Muckerkeide,and Goldman, editors.

* cited by examiner

*Primary Examiner*—Roy D. Gibson
*Assistant Examiner*—H. M. Johnson
(74) *Attorney, Agent, or Firm*—Fenster & Company

(57) ABSTRACT

Performing selective photothermolysis of sub-cutaneous tissue by using a plurality of beams of narrow band electromagnetic radiation, where each of the beams have energy that is insufficient to heat the tissue that they strike to a temperature high enough to destroy such tissue, but by directing the individual beams to overlap at the target sufficient heat is generated to destroy the target tissue.

45 Claims, 3 Drawing Sheets

SELECTIVE PHOTOTHERMOLYSIS

RELATED APPLICATIONS

This application is a U.S. national filing of PCT Application No. PCT/IL99/00658, filed Dec. 2, 1999.

FIELD OF THE INVENTION

The present invention relates to apparatus and a method of selective photothermolysis that allows the destruction of unsightly skin disorders, such as birthmarks, varicose veins, plaque psoriasis and others. According to the invention, the disorders are selectively destroyed without damaging the surrounding healthy tissue.

BACKGROUND OF THE INVENTION

Selective photothermolysis is a method, described by Anderson and Parrish in 1983 ("Selective Photothermolysis: Precise Microsurgery by Selective Absorption of Pulsed Radiation", Science, Vol. 220, pp. 524–527), for destroying certain diseased or unsightly tissue, on or near the skin, with minimal damage to the surrounding healthy tissue. The tissue to be destroyed is generally characterized by significantly greater optical absorption at some wavelength of electromagnetic radiation than the surrounding tissue. The prior art methods include irradiating the target and the surrounding tissue with pulsed electromagnetic radiation, usually visible radiation, that is preferentially absorbed by the target. The energy and duration of the pulses is such that the target is heated to between about 70° C. and about 80° C., at which temperature the proteins of the target coagulate. Because the target absorbs the incident radiation much more strongly than the surrounding tissue, the surrounding tissue absorbs much less heat and for, at least short time periods of exposure, does not reach a temperature to cause damage. However, the surrounding healthy tissue must be prevented from heating up over extended heating period. Extended heating periods are required for larger skin disorders such as varicose veins.

Usually, the radiation source is a laser, for example a flashlamp-pulsed dye laser. A laser source has the advantage of being inherently monochromatic. Other sources include broad band sources used in conjunction with narrow band filters, as described, for example, by Gustaffson in Patent publication. WO 91/15264. A similar device, called the "Photoderm-VL", is manufactured by ESC Medical Systems.

Suitable targets for selective photothermolysis include birthmarks, port-wine stains, spider veins, and varicose veins, all of which tend to be much redder than the surrounding tissue because of their higher concentration of oxyhemoglobin-containing red blood cells.

Anderson and Parrish used light of a wavelength of 577 nanometers, corresponding to the 577 nanometer oxyhemoglobin absorption band. It was subsequently determined (Tian, Morrison, and Kurban, "585 nm for the Treatment of Port-Wine Stains", Plastic and Reconstructive Surgery, vol. 86 no. 6 pp. 1112–1117) that 585 nanometers is a more effective wavelength to use.

One constraint on the pulse duration is that the surrounding tissue must not be heated to the point that it, too, begins to coagulate. As the disorder (hereinafter sometimes referred to as the "target") is heated, heat is conveyed by convection and conduction from the target to the cooler surrounding tissue. To keep the surrounding tissue from being heated to the point of damage, the pulse length in the prior art is kept on the order of the target's thermal relaxation time. For relatively small targets, such as birthmarks, port-wine stains, and spider veins, typical pulse lengths are on the order of hundreds of microseconds. For varicose veins, pulse lengths on the order of milliseconds should be used.

A complication arises in the treatment of varicose veins by selective photothermolysis. The normal tissue surrounding varicose veins typically includes other blood vessels, notably capillaries, that also absorb the incident radiation but, being much smaller than the varicose veins, have much shorter thermal relaxation times. Therefore, heat diffusing from these other blood vessels tends to heat the surrounding tissue to the point of damage to the surrounding tissue and/or to those other blood vessels. The damage to the surrounding tissue may include scarring.

Recently, selective photothermolysis also has been used to treat psoriatic skin tissue. Psoriasis is a non-contagious skin disorder that most commonly appears as inflamed swollen skin lesions covered with silvery white scale. This most common type of psoriasis is called "plaque psoriasis".

Psoriasis comes in many different variations and degrees of severity. Different types of psoriasis display characteristics such as pus-like blisters (pustular psoriasis), severe sloughing of the skin (erythrodermic psoriasis), drop-like dots (guttate psoriasis) and smooth inflamed legions (inverse psoriasis). The degrees of severity of psoriasis are divided into three important categories: mild, moderate and severe.

Skin cells are programmed to follow two possible programs: normal growth or wound healing. In a normal growth pattern, skin cells are created in the basal cell layer, and then move up through the epidermis to the stratum corneum, the outermost layer of the skin. Dead cells are shed from the skin at about the same rate as new cells are produced, maintaining a balance. This normal process takes about 28 days from cell birth to death.

When skin is wounded, a wound healing program, also known as regenerative maturation, is triggered. Cells are produced at a much faster rate, theoretically to replace and repair the wound. There is also an increased blood supply and localized inflammation. In many ways, psoriatic skin is similar to skin healing from a wound or reacting to a stimulus such as infection.

Lesional psoriasis is characterized by cell growth in the alternate growth program. Although there is no wound at a psoriatic lesion, skin cells, also referred to as keratinocytes, behave as if there is. These keratinocytes switch from the normal growth program to regenerative maturation. Cells are created and pushed to the surface in as little as 2–4 days, and the skin cannot shed the cells fast enough. The excessive skin cells build up and form elevated, scaly lesions. The white scale (called "plaque") that usually covers the lesion is composed of dead skin cells, and the redness of the lesion is caused by increased blood supply to the area of rapidly dividing skin cells.

Flash-lamp-pumped pulsed dye laser beams have been used to selectively destroy cutaneous blood vessels. Light passing through the epidermis is preferentially absorbed by hemoglobin, the major chromophore in the blood of the ectatic capillaries of the upper dermis. The radiant energy is converted to heat causing the thermal damage and necrosis in the target. Flash-lamp-pumped pulsed dye laser in general destroy the targeted dermal disorder. The problem is the prevention of damage to the surrounding healthy tissue.

For example, port wine stains are known to be characterized by normal epidermis overlying an abnormal plexus of dilated blood vessels located on a layer in the upper dermis. The predominate endogenous and/or cutaneous chromophores that absorb light at the 585 nanometer wavelength produced by flash-lamp-pumped pulsed dye laser are melanin and hemoglobin. Accordingly, the overlying epidermal pigment layer acts as an optical shield through which the light must pass to reach the underlying lesion such as those caused by port wine stain blood vessels. The absorption of laser energy by the melanin causes localized heating in the epidermis and reduces the light dosage reaching the target thereby decreasing the quantity of heat in the targeted area, leading to sub-optimal blanching of the tissue disorder or necessitating increased time periods of treatment with consequent increased risk of healthy tissue damage, unless steps are taken to protect the healthy tissue.

In the past various cooling methods, ranging from applying ice to the epidermis to spraying the epidermis with a cryogenic gas were used to assure that necrosis due to the applied radiant energy only effects the target and not the surrounding or overlying tissue. See, for example, the article by A. J. Welch et al entitled "Evaluation of Cooling Techniques for the Protection of the Epidermis During ND-YAG Laser Radiation of Skin Neodymium-YAG Laser in Medicine", Stephan N. Joffe, editor (1983). Skin cooling with freon proved effective in less than 30% of the cases, according to the article. A patent showing skin cooling with cryogen is U.S. Pat. No. 5,814,040, the disclosure of which is hereby incorporated herein by reference.

Other prior art cooling methods used to prevent damage to healthy tissue include the use of lens-like contact devices having high thermal conductivity and having a refractive index that enables the optical radiation to be coupled with the epidermis i.e., a refractive index of approximately 1.55. Thus, the contact device is preferably formed of a high density material such as sapphire or other similar optically transparent glass or plastic. See, for example, U.S. Pat. No. 5,595,568, the disclosure of which is hereby incorporated herein by reference.

Accordingly, since skin cooling depends on many uncontrollable factors, those in the art of selective photothermolysis are still searching for systems that destroy the targeted tissue disorder without damaging overlying and surrounding healthy tissue.

SUMMARY OF THE INVENTION

According to an aspect of some preferred embodiments of the present invention there is provided a method and apparatus of selective photothermolysis of a sub-cutaneous target within overlying healthy tissue, comprising: directing a plurality of beams of radiant energy at the target where each of the individual beams is designed to raise the temperatures to a temperature at which the skin is not damaged, for example below 55° C., and where the plurality of beams confluencing at the target raise the temperature of the target sufficiently to cause necrosis i.e., to between 70° and 80° C.

According to an aspect of some preferred embodiments of the present invention there is provided a device for selective photothermolysis of a sub-cutaneous target within surrounding healthy tissue. Preferably the device comprises: an electromagnetic pulse gererator that generates at least two pulsed beams of narrow band or substantially monochromatic electromagnetic radiation, each of said at least two beams being aimed at the target from a different external position, but overlapping at the target or being aimed at the target from the same external position but being aimed substantially sequentially.

A method and apparatus of an aspect of the present invention is based on the use of a plurality of radiant energy beams, each having insufficient energy to heat the tissue traversed by the beam enough to cause necrosis, but nonetheless heating the disorder of a targeted area sufficiently to destroy the disorder due to the combined energy of two or more beams. The two or more beams can strike the target either substantially simultaneously or substantially sequentially. In the context of the present invention, the pulse of narrow band light per individual beam used to destroy the target may be of lower power and shorter duration than in the prior art, because the target is heated by the combined energy of a plurality of beams, in accordance with a preferred embodiment of the invention.

The beams of radiation used to heat the target can preferably be generated by a laser that operates at a wavelength between about 550 nanometers and about 800 nanometers. Alternatively or additionally, the beams can be generated by pulsing light from a high intensity lamp through a suitable wavelength selection device, such as a narrow band filter or a monochromator.

A device, according to a preferred embodiment of the present invention, uses at least two pulsed beams of the narrow band width that traverse the target-overlying epidermis at different areas, but either substantially overlap at the target or arrive substantially sequentially at the target to ensure that the overlying tissue is not unduly heated and that the target is heated sufficiently to destroy the tissue disorder.

Additionally, in conjunction with the multiple beams operating at the target optionally the skin may be cooled, to further avoid overheating of the skin; such cooling enables the use of beams with higher heat producing content.

Preferred apparatus for selective photothermolysis of a sub-cutaneous target tissue to correct skin disorders, comprises:

at least two narrow band electromagnetic radiation beams which approach the target substantially sequentially so that the heat generated by each of the beams is insufficient to significantly damage the surrounding tissue but the combination of beams of the target area causes necrosis, especially when the target area's relocation time is longer than the relaxation time of the surrounding tissue. Relaxation time as used herein is the time required to dissipate the beam-generated heat.

Other preferred apparatus for selective photothermolysis of a sub-cutaneous target tissue to correct skin disorders comprises:

at least two narrow band electromagnetic radiation beams which approach the target substantially sequentially so that the heat generated by each of the beams is insufficient to significantly damage the surrounding tissue but the combination of beams of the target area causes necrosis, especially when the target area's relocation time is longer than the relaxation time of the surrounding tissue. Relaxation time as used herein is the time required to dissipate the beam-generated heat.

Preferably, the apparatus may include a sensing unit for sensing the temperature of said skin. Preferably, the sensing unit includes at least one optical sensor for sensing the temperature of said skin, said at least one optical sensor preferably receives infra-red radiation emanating from an area of said skin where a single beam strikes the skin. The infra-red radiation is received through at least one optical element, which optical element senses the intensity of said infra-red radiation and provides signals indicative of said intensity to a controller. In a preferred embodiment of the invention the at least one optical sensor includes an infra-red light sensitive photo-diode. Alternatively or additionally, the sensor unit may include at least one contact temperature sensor for contacting said skin to sense the temperature of said skin, and for providing said controller with signals indicative of said temperature. Preferably the at least one contact temperature sensor comprises a thermistor.

In a preferred embodiment of the invention, the apparatus includes:

a controller unit which controls a source or sources which provide the plurality of beams of electromagnetic radiation, for controlling the sequence of activation of said source of beams of electromagnetic radiation responsive to said sensed temperature.

Preferably, the controller unit has a data input port capable of receiving data determining at least one treatment parameter selected from a plurality of treatment parameters for coordinating the timing and the duration of activation of all or selected ones of said beams of narrow band electromagnetic radiation.

In another preferred embodiment of the invention the apparatus includes: a housing for said source or sources of said narrow band electromagnetic radiation; a pump attached to said housing and controlled by said controller for controllably pumping a cooler gas into said housing to displace air heated by said beams with air having a temperature lower than the temperature of said heated air, to provide supplemental aid in the prevention of overheating of healthy tissue surrounding a sub-cutaneous tissue disorder. Preferably, the pump is activated by said controller when said skin has reached a predetermined temperature after said beams are transmitted. Preferably, the controller unit is capable of determining at least one treatment parameter selected from a plurality of treatment parameters for coordinating the timing and the duration of selective activation of said beams of narrow band electromagnetic radiation.

In a preferred embodiment of the invention, the controller unit includes a storage device on which said plurality of treatment parameters are stored, said storage device may be removable from said controller for changing the value of at least one of said plurality of treatment parameters, prior to reconnecting said storage device to said controller. At least certain of the parameters determine how many beams are to be activated. Preferably, the storage device is selected from a memory device such as, but not limited to, a flash memory device, a magnetic bubble memory device, an EPROM memory device, an EEPROM memory device, an optical memory device, an opto-magnetic memory device and a magnetic memory device.

In a preferred embodiment of the invention, the apparatus includes a cooling unit suitably attached to said housing and controlled by said controller for controllably cooling surrounding tissue, to augmentally prevent healthy tissue surrounding the tissue disorder from overheating. Preferably, the cooling unit is activated by said controller when said skin has reached a predetermined temperature after said heat source is energized.

There is thus provided, in accordance with a preferred embodiment of the invention, apparatus for selective photothermolysis of sub-cutaneous target tissue, the apparatus comprising a plurality of beams of narrow band electromagnetic radiation, each of the beams having energy that is insufficient to heat tissue upon which is falls to a temperature high enough for tissue damage; and a beam director directing said beams to substantially overlap beneath the skin at a target, said combination of light beams due to the overlapping being capable of causing the target area to heat sufficiently to cause tissue damage; thus destroying the cause of skin disorders. Preferably, the beam director directs the beams to overlap substantially simultaneously. Alternatively or additionally the beams are caused to overlap substantially sequentially. In a preferred embodiment of the invention, the narrow band electromagnetic radiation is a monochromatic light. Preferably, the plurality of beams of light is produced by at least a single source. Alternatively or additionally, the light is produced by a plurality of light sources. Preferably, the apparatus, includes pulsing apparatus for providing pulses of said light. In a preferred embodiment of the invention the light is laser light. Preferably, the laser light has a wavelength in the range of 550–800 nanometers. Alternatively, the light is provided by a flash-lamp providing pulses of light or alternatively, the monochromatic light is derived from filtering broad band light with a narrow band filter. Preferably, a plurality of light sources are provided. In a preferred embodiment of the invention, a cooling device for cooling tissue surrounding the target area during and/or after the photothermolysis is provided. Preferably, the cooling device comprises a housing for said light, said housing sealing said target area and surrounding tissue, and pump means for replacing warmed air in said housing with cooler air. In a preferred embodiment of the invention, the apparatus includes at least a temperature monitor monitoring the temperature of air in said housing. Additionally or alternatively, at least a temperature monitor monitoring the temperature of the surrounding tissue is provided. Alternatively or additionally, at least a temperature monitor for monitoring the temperature of the target is provided. In a preferred embodiment of the invention, the apparatus includes control apparatus for controlling the applications of the electromagnetic light responsive to monitored temperatures. Preferably, the control apparatus controls the application time and heat content of the light responsive to the monitored temperatures.

There is further provided a method for selective photothermolysis of sub-cutaneous target tissue, comprising: producing a plurality of beams of narrow band electromagnetic radiation, each of the beams having energy that is insufficient to heat tissue upon which is falls to a temperature high enough for tissue damage; and directing said beams so that there is an overlapping of said plurality of beams at the target tissue, causing the target tissue to heat sufficiently to cause tissue damage and thereby destroy the cause of the skin disorder. Preferably, the narrow band electromagnetic radiation is a monochromatic light. Preferably, the method includes substantially simultaneously emitting a plurality of beams comprising said light from a single source. Alternatively or additionally, substantially simultaneously or sequentially emitting said monochromatic light from a plurality of light sources. In a preferred embodiment of the invention, the method includes providing pulses of said monochromatic light. In a further preferred embodiment of the invention, the light is laser light. Preferably, the laser light has a wavelength in the range of 550–800 nm. Alternatively or additionally, the method includes deriving said monochromatic light from broad band light and a narrow band filter. Preferably, the plurality of light beams are produced by a plurality of monochromatic light sources. In a preferred embodiment of the invention, the method includes cooling tissue surrounding the target area during and/or after the photothermolysis. Preferably, the cooling comprises trapping the air around the target area and surrounding tissue, and replacing trapped warned air with cooler air. In a preferred embodiment of the invention, the method includes monitoring the temperature of the trapped air. Alternatively or additionally, the method includes monitoring the temperature of the surrounding tissue; and/or monitoring the temperature of the target and controlling the application of the electromagnetic radiation responsive to said monitored temperature or temperatures. Preferably, controlling the application comprises controlling the application time and heat content of the electromagnetic radiation responsive to said monitored temperature or temperatures. Alternatively or additionally, controlling the application comprises controlling the application time and heat content responsive to stored parameters. In a preferred embodiment of the invention, cooling includes contacting tissue on which the radiation falls with a device having good thermal conductivity and a refractive index enabling optical radiation to be coupled therethrough. Alternatively or additionally, cooling includes cooling the skin with a cryogen.

BRIEF DESCRIPTION OF THE DRAWINGS

The principles and operation of a selective thermolysis according to different aspects of the invention may be better understood as herein described, by way of example only, with reference to the accompanying drawings and description; wherein.

DETAILED DESCRIPTION OF THE PREFERRED EMBODIMENTS

An aspect of the present invention is a method and device for selective photothermolysis of various sized targets. Specifically, the present invention can be used to remove varicose veins and or port wine stains, psoriasis and similar unsightly tissue with equal facility and with minimal damage to the surrounding healthy tissue.

Figure 1:
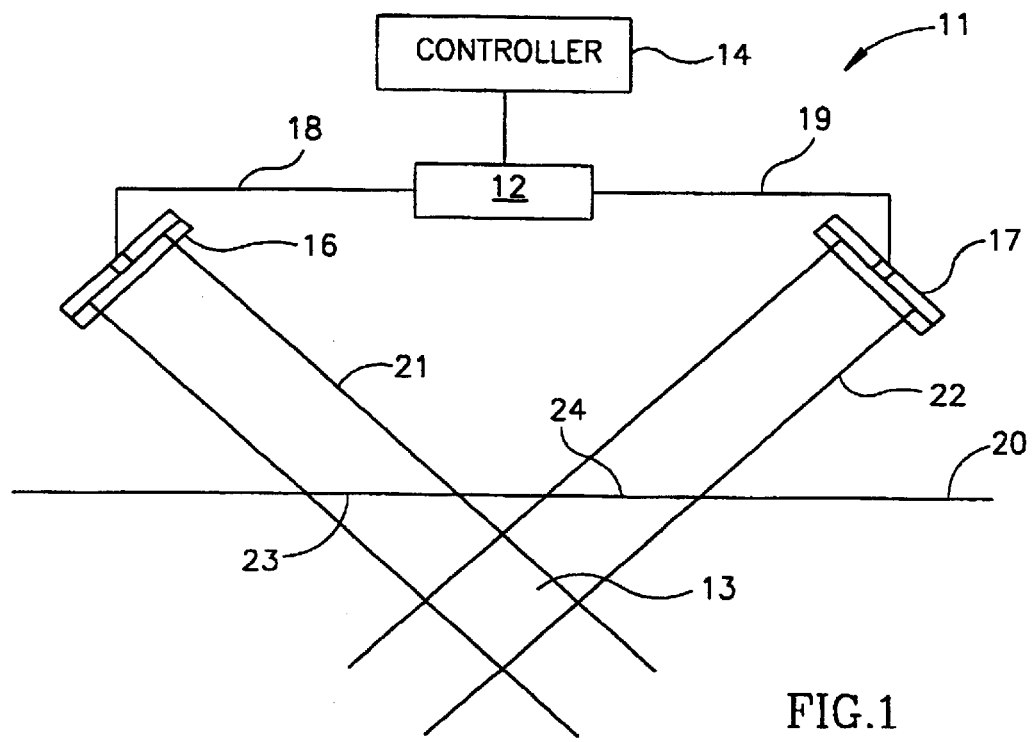
FIG. 1 is a schematic diagram of a preferred embodiment of a device according to the present invention in which a single source of monochromatic light produces beams that overlap on the target.

Referring now to the drawings, FIG. 1 is a schematic diagram of a basic preferred embodiment of the present invention. There is shown in FIG. 1 a system 11 which comprises a single source of monochromatic light 12. Preferably, the monochromatic light source provides a laser beam. Alternatively, the source could be the source of broad-band (white) light operated in conjunction with a filter (not shown) to filter out all of the white light, except for the desired monochromatic light. The monochromatic light, preferably, is at a wavelength of between 550–800 nanometers, directed at a target 13 through the epidermis and surrounding tissue.

A control device such as controller 14 controls the operation of the source 12 and also may supply power to the source. The controller turns on the monochromatic light source 12 for controlled periods of time so that pulsed light is emitted from the system 11.

FIG. 1 shows the source 12 coupled to light emitters 16 and 17 through fiber-optic cables, for example, shown at 18 and 19 respectively. Preferably, the source 12 provides laser beams using a pulsed dye flash-lamp, for example such as the Sclero Laser, manufactured by Candela Corp. of Wayland, Md. Monochromatic light beams are shown at 21 and 22, issuing from the light emitters 16 and 17. The light beams 21, 22 are shown as individually striking the skin 20 at areas 23 and 24 respectively, and overlapping at target 13.

Figure 2:
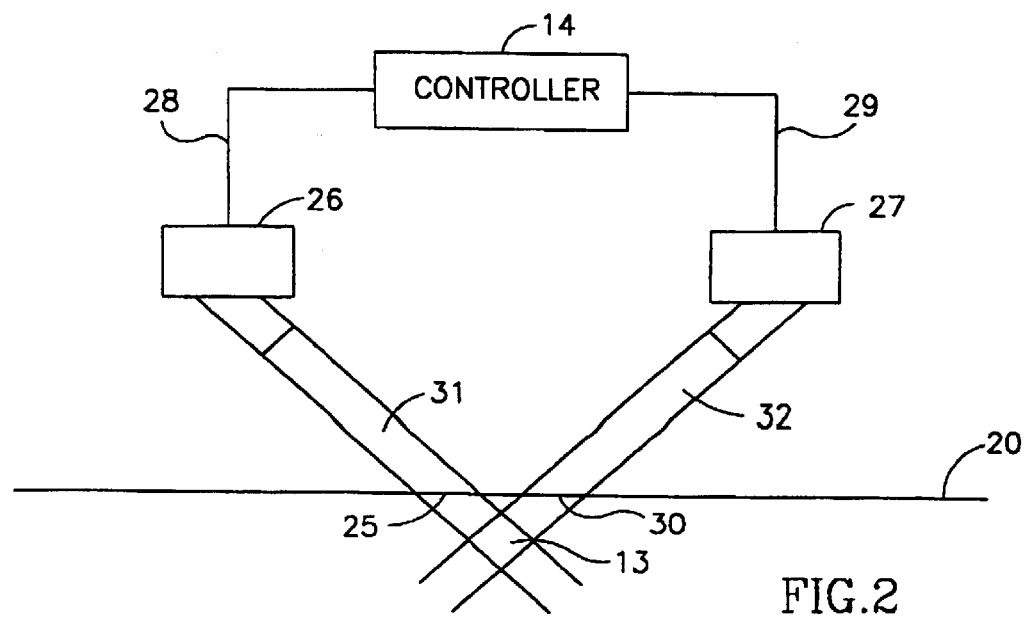
FIG. 2 is a schematic diagram of a preferred embodiment of a device according to the present invention in which a separate source of monochromatic light is provided for each of the beams.

FIG. 2 shows an alternative preferred embodiment of the invention in which a separate source of monochromatic lighting is provided for each of the beams under the direction of the controller. Controller 14 is shown coupled to light sources 26, 27 through cables 28, 29. The light sources provide monochromatic light beams 31, 32 which strike the epidermis 20 at areas 25, 30, penetrate the epidermis and overlap at the target area 13.

In the embodiment shown in FIG. 2 the beams are not focused at the target area.

Combinations of single sources of multiple beams with individual sources for each of the beams can be provided within the scope of the present invention. Thus, both single sources and multiple sources can be in use simultaneously. In both FIG. 1 and FIG. 2 the light beams preferably do not have enough energy when a single light beam strikes the patient to heat the tissue that it traverses to a temperature that will cause tissue damage. However, when the multiple beams strike the target, then, because of the additive heat energy of the multiple beams, there is sufficient energy to heat the target to cause tissue damage and necrosis. Accordingly, the tissue disorder can be eliminated by combining beams which by themselves do not have sufficient energy to cause tissue damage, but in unison with other beams, do have enough energy to cause necrosis.

Cooling of surrounding tissue may be necessary where the combined beams require such a high heat content to destroy the disorder, that without the cooling the surrounding tissue would be damaged even by a single beam. As used herein, the term "insufficient to cause tissue damage" or "insufficient to cause necrosis" means that such insufficiency is determined in the presence of any cooling of the skin that may be applied.

When attacking large disorders such as varicose veins, a multiplicity of beams can be directed at the target to assure sufficient power at the target to damage the largest tissue causing necrosis, without damaging surrounding tissue. Such a multiplicity of beams is shown, for example, in FIG. 3 which is a plan view of a plurality of beams striking the skin from different angles.

Figure 3:
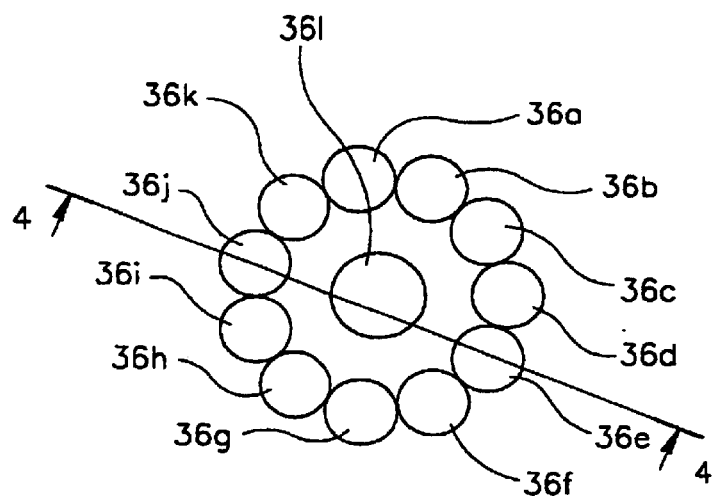
FIG. 3 is a plan view of a preferred embodiment of the invention wherein a plurality of monochromatic light beams are depicted striking the skin.

The beams are all directed toward the target and strike the epidermis at different positions surrounding the target area. For example, there is shown eleven beams; however, the number of beams is limited only by the space surrounding the target area. Beams shown in FIG. 3 are, for example, the twelve beams 36a–36l. The beams are shown in a circular arrangement. They could be in any geometrical arrangement. While a single beam is shown in the center, multiple beams could also be provided within the outer circle of beams.

Figure 4:
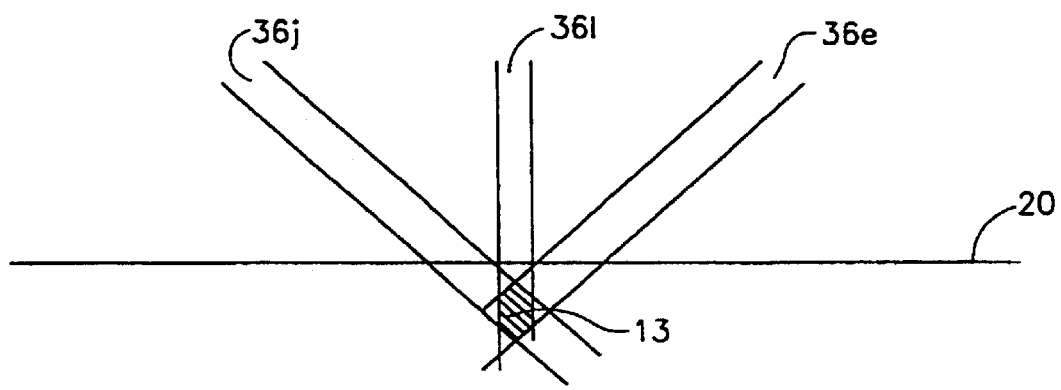
FIG. 4 is a sectional view of the light beams of FIG. 3 taken along line 4—4 of FIG. 3 looking in the direction of the arrows and showing the beams overlapping on the target.

FIG. 4 shows a cross-sectional view of three of the beams of FIG. 3 overlapping on the target. Thus, FIG. 4 shows beams 36j, 36e and 36l, penetrating the epidermis 20 and striking the target at 13. While only three beams are shown in the cross-sectional view, the number of the overlapping beams of FIGS. 3 and 4 include the eleven beams shown. The beams preferably are pulsed to further assure that the surrounding tissue is not damaged.

Other measures can be taken to assure that the surrounding tissue is not damaged. If cooling is used, then the heat threshold at which damage occurs may be increased. However, in essence, only the confluence of multiple beams has sufficient energy to cause damage in the presence of the cooling. In general, however, there is insufficient heat generated by the individual beams to cause damage to the healthy tissue in the volume surrounding the tissue disorder. Therefore, other measures are not generally necessary.

Figure 5:
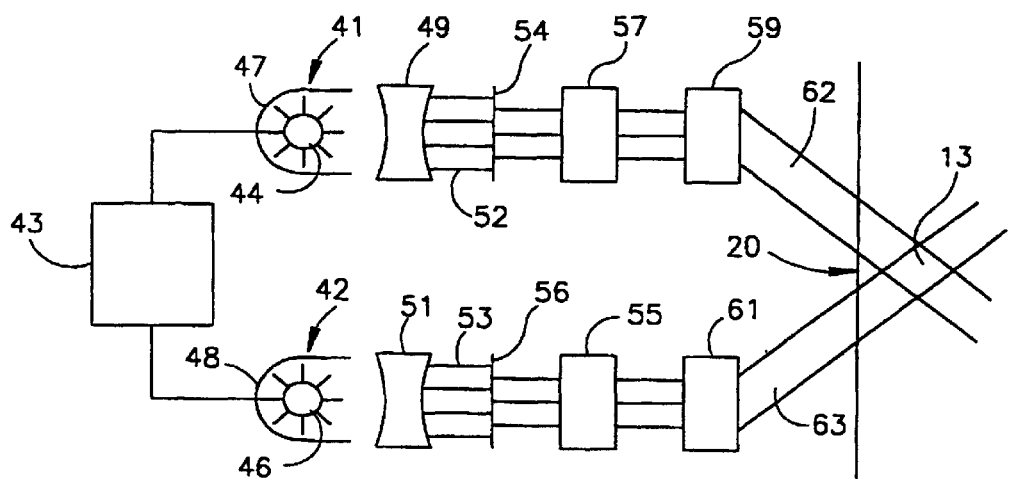
FIG. 5 shows another preferred embodiment of the invention, wherein the plurality of monochromatic beams are derived from sources of white light.

FIG. 5. is a schematic diagram of another preferred embodiment of the present invention. In this embodiment, the sources of the plurality of monochromatic beams are shown as being two independent white light broad band light sources 41 and 42. The sources are under the control of controller 43. Light sources 41 and 42 comprise lamps 44 and 46, within parabolic reflectors 47 and 48. The broadband light is directed by the parabolic reflectors to concave lenses 49 and 51. The concave lenses provide essentially parallel light beams indicated at 52 and 53. The light beams are directed to shutters 54 and 56. The shutters open and close to provide the pulsed light going to light filters 57 and 55. The light filters act to filter out all light except for light preferably at a wavelength which is most efficient for destroying the particular tissue disorders; for example, for the treatment of port-wine stains a wavelength of 585 nanometers is used. The light from the filters 57 and 55 passes to light directors 59 and 61. The light directors direct beams 62 and 63 to strike the epidermis 20 of the patient and overlap at the sub-cutaneous target area 13.

Alternatively, one or both of the beams 62 or 63 can be a laser beam having a wavelength in the range of 565–800 nm. Also, while two sources are shown here, a plurality greater than two sources can be utilized. For more details on the shutter and the filter, see for example U.S. Pat. No. 5,759,200, issued on Jun. 2, 1998, the disclosure of which is hereby incorporated herein by reference. Alternatively, one or both of the beams can be flash-lamp beams, eliminating the need for the shutter.

The intensity of the light coming from the two individual sources is sufficient to heat the surrounding tissue preferably to a temperature below 55 degrees, a temperature insufficient to damage the healthy tissue. As an added safety measure, the light in beams 62 and 63 is pulsating, further reducing the likelihood that the surrounding tissue will be damaged. If necessary, the skin can be cooled, as described above. Alternatively or additionally, the controller 67 interrupts the beams of light when the temperature of the target reaches between 70 and 80 degrees C.

Figure 6:
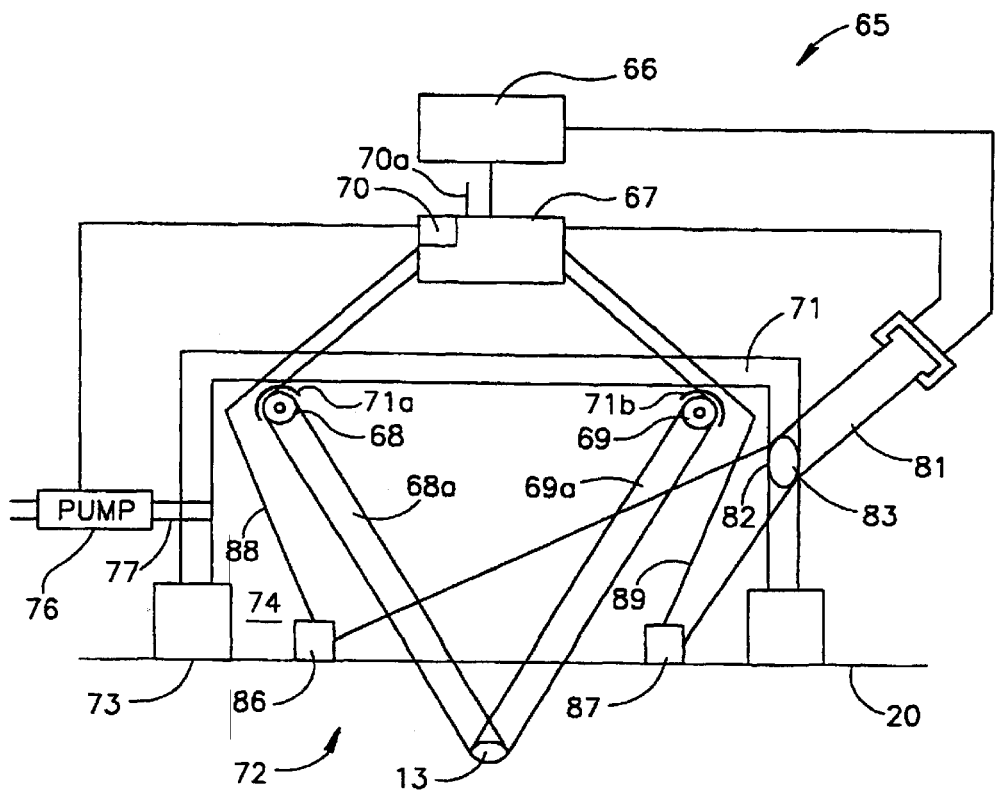
FIG. 6 schematically shows a device according to a preferred embodiment of another aspect of the invention, including a plurality of sources of monochromatic beams in a housing containing additional auxiliary equipment.

FIG. 6 shows a cooling embodiment wherein the heat sources are enclosed in a housing which includes auxiliary cooling apparatus to further assure that the surrounding tissue will not be damaged during the treatment of the target. The apparatus 65 of FIG. 6 includes a power source 66 connected to a controller 67, which controls the two light sources 68 and 69 (more may be present). The light sources are enclosed in a housing 71. The housing is preferably made of a thermally insulating material such as a high temperature plastic, ceramic material, or any other suitable, thermally insulating material. Housing 71 has an opening 72 which is placed on the surface of the tissue to be treated; i.e., on the surface of the epidermis 20. Preferably suitable reflectors 71*a*, 71*b* are attached to light sources 68 and 69 respectively, to direct beams of light energy 68*a* and 69*a* to traverse the overlying tissue and overlap on the target tissue.

Apparatus 65, preferably includes a sealing gasket 73 made from soft rubber or the like for sealing the contact with the skin 20 when opening 72 of housing 71 is placed on the skin. When housing 71 is lightly pressed onto the skin, a sealed cavity 74 is formed. Sealed cavity 74 includes a volume of air which is enclosed between the epidermis 20 and the housing 71. The light source may be a laser source or a white light source. The apparatus 65 is shown as including a pump 76 connected through the housing 71 by a tube 77 for pumping cooler air or cooled gas into cavity 74. The pump, in conjunction with the housing, further prevents overheating the skin by replacing the air at the surface of the skin with cooler air. Since the temperature of the air at the skin surface normally continues to increase with time due to conduction, convection and radiation, such cooling helps to avoid post-illumination tissue damage.

It is noted that while a pump is shown, other means for cooling may be used, for example a cryogen gas dispenser or contact devices such as described hereinabove may be used. The apparatus 65 preferably includes sensing units for sensing the temperature of the skin in the cavity 74. The sensing unit may include an optical sensor 81 and a collimating optical element 82. Preferably, the optical element 82 is attached within an aperture 83 of housing unit 71. The optical element 82 and optical sensor 81 are aligned such that the field of view of the sensor unit covers a substantial portion of the skin under opening 72, but preferably does not include any part of housing 71.

Preferably, the sensing unit 81 is an infrared sensing unit such as the model A53,367 infrared thermometer commercial available from Edmund Scientific Co., New Jersey U.S.A. However, any other suitable optical sensing unit can be used, provided that it has sufficient sensitivity in the relevant range of temperatures approximately 30° to 80° C. The lens 82 is an infrared lens, substantially transparent to infrared radiation.

It is noted that while a preferred embodiment of the invention shown in FIG. 6 has an optical element that is a collimating infrared lens 82, other optical elements such as, but not limited to an optical window, holographic lamp, composite lens, a micro-lens array or any other optical element may be used that is suitable for collimating infrared radiation in the spectral band necessary for sensing of the temperature of the skin's surface within the lens's field of view.

It is further noted that while the embodiment of the invention illustrated in FIG. 6 has only one sensing unit 81, including one optical sensor 82, other preferred embodiments of the present invention may be constructed to include more than one optical unit. This may be required to include a wider portion of the skin surface 20 or for other alignment or other manufacturing considerations. In such a case, additional apertures could be made within the housing 71.

Power source 66 is suitably connected to controller 67 to provide power to the controller. Controller 67 is also preferably connected to sensing unit 81 for receiving signals from the sensing unit. The signals represent the temperature of the surface of the portion of the skin which is included in the field of view. Controller 67 is also preferably connected to pump 76 along with the power source 66 for providing power and controlling the operation of the pump.

In a preferred embodiment of the invention, power source 66 is an electrical power source such as DC power supply connectable to a mains AC power socket. However, it can also be also one or more disposable batteries, one of more rechargeable batteries, at least one capacitor and an electronic control circuit or any other suitable electrical power source.

Additionally, power source 66 may be included within controller 67 or may comprise a plurality of power sources not shown, each capable of providing different voltages and/or current level. For example, one power source, not shown, may be used for powering controller 67, while another power source may be used for energizing the light sources 68 and 69, and the pump 76.

To use apparatus 65 the user places opening 72 adjacent to the skin 20 to be treated and lightly presses apparatus 65 against the skin to achieve sealing of the air volume within cavity 74 by sealing gasket 73. The user then activates the treatment sequence by pressing a button or a suitable switch (not shown) to cause controller 67 to activate the light sources, producing light pulses of 1–35 milliseconds duration that irradiates the skin tissue with monochromatic light of approximately 0.5–10 joules per sq. cm.

Optical sensor 81 preferably senses the intensity of the infrared radiation emitted from the skin 20 within the field of view and sends signals to controller 67, which processes the signals, to determine the temperature of the skin within the field of view. When the temperature of the skin within the field of view reaches a certain predetermined temperature, for example about 55° C., controller 67 activates the pump 76 to assure the skin and surrounding tissue does not heat up sufficiently to cause necrosis of healthy tissue.

The pulses of the monochromatic light are approximately 1.0 milliseconds to 5 milliseconds long and irradiate the target with narrow band light having a power density of 1.0–10 joules per sq. cm., when overlapping. Overlapping narrow band radiation is selectively absorbed by the target tissue, for example the blood vessels and capillaries within the targeted skin disorder, thus selectively heating and coagulating the blood vessels and capillaries of the tissue of the target without damaging the surrounding skin tissue. After a set amount of time, or when the skin is at a predetermined temperature, controller 67 activates the pump 76, which pumps air at room temperature into the cavity 74 of housing 71 through tube 77 in order to cool the skin and prevent the skin from reaching a temperature sufficient to cause coagulation. The optimum time of pump activation may be determined empirically.

Alternatively or additionally to the infrared temperature measuring device, contact temperature sensors may be used such as shown at 86 and 87. Sensors 86, 87 are connected to controller 67 through conductors 88 and 89. While two skin temperatures contact sensors are shown, in operation fewer or more contact sensors could be used. It is further noted that the contact temperature sensors must have a fast enough response time so as to sense the temperature of the surface of the skin as the temperature of the skin rises to enable controller 67 to timely activate the pump or other cooling unit. This type of temperature response is obtained by using thermistors or other suitable temperature contact sensors having a minimal thermal mass.

As indicated in FIG. 6, controller 67 includes a storage device 70 which stores a plurality of treatment parameters. The controller in such a case operates to control the operation of the photothermolysis apparatus, based on the stored parameters. The storage device may be removable from the controller for changing a parameter. At least certain of the parameters may determine the number of beams to activate.

The controller, for example, causes the light sources 68 and 69 to operate in a pulsating manner. When the temperature as determined by the sensor 81 reaches a value stored in storage unit 70, pump 76 is operated and/or the beams are turned off. The storage unit may be a memory device such as a flash memory, magnetic bubble memory, EPROM memory, EEPROM memory, optical memory, opto-magnetic memory or a magnetic memory. The controller can also cause more than two beams to be directed at the target in response to stored parameters. The parameters used by the controller may be inputted to the controller through input port 70a as an alternative or in addition to the parameters in the storage unit 70.

It will be appreciated by persons skilled in the arts that the invention is not limited to what has been disclosed hereinabove, and illustrated in the drawings. Also, while the invention has been described with respect to a limited number of embodiments, it will be appreciated that many variations, modifications and other adaptations made be made. In addition, as pointed out hereinabove, laser or other monochromatic sources or wide-band sources with suitable filters can be used as the sources of the light beams. Furthermore, each of the above described embodiments includes a plurality features which may be transferred from embodiment to embodiment.

It should be understood that features from one embodiment may be added to or to or may replace features in another embodiment. Furthermore, some of the features, while desirable, are certainly not essential, and may be omitted in some preferred embodiments.

The terms "comprise", "include" or "have" or their conjugates as used herein mean "including but not necessarily limited to".

What is claimed is:

1. Apparatus for selective photothermolysis of subcutaneous target tissue, the apparatus comprising:
    at least one source providing a plurality of beams of narrow band electromagnetic radiation;
    a beam director that directs said beams to exit the apparatus, each of said beams exiting the apparatus at a different angle; and
    a controller adapted to adjust the at least one source and the means for directing such that each of the beams, has an energy that is insufficient to heat tissue upon which it falls to a temperature high enough for tissue damage, said plurality of beams due to overlapping thereof being capable of causing the target area to heat sufficiently to destroy the target tissue,
    wherein an exit of the apparatus, through which said beams pass is adapted to be placed against the skin of a patient.

2. The apparatus of claim 1 wherein the beam director directs the beams to overlap substantially simultaneously.

3. The apparatus of claim 1 wherein the overlapping is substantially sequentially.

4. The apparatus of claim 1 wherein said at least one source comprises a flash lamp and a narrow band filter that filters broad band light emitted by said flash lamp.

5. The apparatus of claim 1 wherein the beam radiation is incoherent.

6. The apparatus of claim 1 wherein said at least one source comprises at least one laser.

7. The apparatus of claim 6 where the laser beams have a wavelength in the range of 550–800 nanometers.

8. The apparatus of claim 1 wherein said at least one light source comprises a single light source which produces said plurality of beams.

9. The apparatus of claim 1 wherein said at least one light source comprises a plurality of light sources which produce said plurality of beams.

10. The apparatus of claim 1 including pulsing apparatus for providing pulses of said beams.

11. The apparatus of claim 1 including a cooling device for cooling tissue surrounding the target area during and/or after the photothermolysis.

12. The apparatus of claim 1 wherein the narrow band electromagnetic radiation is in the wavelength range of 550 to 800 nanometers.

13. Apparatus for selective photothermolysis of subcutaneous target tissue, the apparatus comprising:
- at least one source providing a plurality of beams of narrow band electromagnetic radiation;
- a beam director that directs said beams to exit the apparatus, each of said beams exiting the apparatus at a different angle;
- a controller adapted to adjust the at least one source and the means for directing such that each of the beams, has an energy that is insufficient to heat tissue upon which it falls to a temperature high enough for tissue damage, said plurality of beams due to the overlapping thereof being capable of causing the target area to heat sufficiently to destroy the target tissue,
- a housing for said plurality of beams;
- a seal to seal said housing to said target area and surrounding tissue; and
- pump means for replacing warmed air in said housing with cooler air.

14. The apparatus of claim 13 wherein said narrow band electromagnetic radiation is a monochromatic light.

15. The apparatus of claim 13 wherein said at least one source comprises at least one flash-lamp.

16. The apparatus of claim 13 including at least a temperature monitor monitoring the temperature of air in said housing.

17. The apparatus of claim 13 including at least a temperature monitor monitoring the temperature of the surrounding tissue.

18. The apparatus of claim 13 including at least a temperature monitor for monitoring the temperature of the target area.

19. The apparatus of claim 17 wherein the controller controls the applications of the plurality of beams responsive to monitored temperatures.

20. The apparatus of claim 19 wherein the controller controls the application time and heating capability of the plurality of beams responsive to the monitored temperatures.

21. Apparatus for selective photothermolysis of subcutaneous target tissue, the apparatus comprising:
- at least one source providing a plurality of beams of narrow band electromagnetic radiation;
- a beam director that directs said beams to exit the apparatus, each of said beams exiting the apparatus at a different angle; and
- a controller adapted to adjust the at least one source and the means for directing such that each of the beams, has an energy that is insufficient to heat tissue upon which it falls to a temperature high enough for tissue damage, said plurality of beams due to overlapping thereof being capable of causing the target area to heat sufficiently to destroy the target tissue,
  - wherein the plurality of beams is not focused at the target area.

22. Apparatus for selective photothermolysis of subcutaneous target tissue, the apparatus comprising:
- at least one source providing a plurality of beams of narrow band electromagnetic radiation;
- a beam director that directs said beams to exit the apparatus, each of said beams exiting the apparatus at a different angle; and
- a controller adapted to adjust the at least one source and the means for directing such that each of the beams, has an energy that is insufficient to heat tissue upon which it falls to a temperature high enough for tissue damage, said plurality of beams due to overlapping thereof being capable of causing the target area to heat sufficiently to destroy the target tissue,
  - wherein the narrow band electromagnetic radiation is in the visible and infrared spectrum.

23. A method for selective photothermolysis of subcutaneous target tissue, the method comprising:
- producing a plurality of beams of narrow band electromagnetic radiation, each of the beams having energy that is insufficient to heat tissue which it impinges to a temperature high enough for tissue damage; and
- directing said beams so that there is a substantial overlapping of said plurality of beams at the target tissue, without overlapping at the skin surface, said overlapping of beams causing the target tissue to heat sufficiently to cause tissue damage wherein said overlapping occurs substantially sequentially.

24. The method of claim 23 wherein said narrow band electromagnetic radiation is a monochromatic light.

25. The method of claim 24 including substantially simultaneously emitting a plurality of beams comprising said monochromatic light from a single source.

26. The method of claim 24 including substantially simultaneously emitting said monochromatic light from a plurality of light sources.

27. The method of claim 24 including providing pulses of said monochromatic light.

28. The method of claim 24 wherein said light is laser light.

29. The method of claim 28 where the laser light has a wavelength in the range of 550–800 nm.

30. The method of claim 23 including deriving said beams from broad band light and a narrow band filter.

31. The method of claim 23 wherein the beam radiation is incoherent.

32. The method of claim 23 including cooling tissue surrounding the target tissue during and/or after the photothermolysis.

33. The method of claim 32 wherein cooling includes contacting tissue which the radiation impinges with a device having good thermal conductivity and a refractive index enabling optical radiation to be coupled therethrough.

34. The method of claim 32 wherein cooling includes cooling the surrounding tissue with a cryogen.

35. The method of claim 32 wherein cooling comprises trapping the air around the target tissue and surrounding tissue, and replacing trapped warmed air with cooler air.

36. The method of claim 35 including monitoring temperature of said trapped air.

37. The method of claim 23 including monitoring temperature of tissue surrounding said target tissue.

38. The method of claim 37 including applying the beams of electromagnetic radiation responsive to said monitored temperature.

39. The method of claim 38 wherein applying comprises controlling application time and heating capability of the beams of electromagnetic radiation responsive to said monitored temperature.

40. The method of claim 38 wherein applying comprises controlling application time and heat content of the beams of electromagnetic radiation responsive to stored parameters.

41. The method of claim 23 including monitoring the temperature at the target tissue.

42. The method of claim 41 including applying the beams of electromagnetic radiation responsive to said monitored temperature.

43. The method of claim 42 wherein applying comprises controlling application time and heating capability of the beams of electromagnetic radiation responsive to said monitored temperature.

44. The method of claim 23 wherein the beams are not focused at the target area.

45. A method for selective photothermolysis of subcutaneous target tissue, the method comprising:
   producing a plurality of beams of narrow band electromagnetic radiation, each of the beams having energy that is insufficient to heat tissue which it impinges to a temperature high enough for tissue damage;
   directing said beams so that there is a substantial overlapping of said plurality of beams at the target tissue, without overlapping at the skin surface, said overlapping of beams causing the target tissue to heat sufficiently to cause tissue damage; and
   trapping the air around the target tissue and surrounding tissue, and
   replacing trapped warmed air with cooler air.

* * * * *